(12) United States Patent
Shinagawa (10) Patent No.: US 9,205,033 B2
(45) Date of Patent: Dec. 8, 2015

(54) COMPOSITE SPHERICAL POLYMER PARTICLES AND THEIR PRODUCTION PROCESS, AND COSMETICS USING THE SAME

(75) Inventor: Yukio Shinagawa, Chuo-Ku (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 656 days.

(21) Appl. No.: 12/586,252

(22) Filed: Sep. 18, 2009

(65) Prior Publication Data

US 2010/0233105 A1  Sep. 16, 2010

(30) Foreign Application Priority Data

Mar. 16, 2009  (JP) ................. 2009-063292

(51) Int. Cl.
| | | |
|---|---|---|
| A61K 8/02 | (2006.01) | |
| A61K 8/19 | (2006.01) | |
| A61K 8/27 | (2006.01) | |
| A61K 8/29 | (2006.01) | |
| A61K 8/81 | (2006.01) | |
| A61Q 1/12 | (2006.01) | |
| B82Y 5/00 | (2011.01) | |
| B82Y 30/00 | (2011.01) | |
| C09C 1/04 | (2006.01) | |
| C09C 1/24 | (2006.01) | |
| C09C 1/30 | (2006.01) | |
| C09C 1/36 | (2006.01) | |
| C09C 1/48 | (2006.01) | |
| C09C 3/10 | (2006.01) | |
| A61Q 1/10 | (2006.01) | |
| A61Q 17/04 | (2006.01) | |

(52) U.S. Cl.
CPC . *A61K 8/19* (2013.01); *A61K 8/025* (2013.01); *A61K 8/0283* (2013.01); *A61K 8/27* (2013.01); *A61K 8/29* (2013.01); *A61K 8/8152* (2013.01); *A61Q 1/12* (2013.01); *B82Y 5/00* (2013.01); *B82Y 30/00* (2013.01); *C09C 1/043* (2013.01); *C09C 1/24* (2013.01); *C09C 1/3072* (2013.01); *C09C 1/3676* (2013.01); *C09C 1/48* (2013.01); *C09C 3/10* (2013.01); *A61K 2800/413* (2013.01); *A61K 2800/43* (2013.01); *A61K 2800/654* (2013.01); *A61Q 1/10* (2013.01); *A61Q 17/04* (2013.01); *C01P 2002/84* (2013.01); *C01P 2004/04* (2013.01); *C01P 2004/64* (2013.01); *C01P 2006/22* (2013.01)

(58) Field of Classification Search
None
See application file for complete search history.

(56) References Cited

U.S. PATENT DOCUMENTS

| | | | |
|---|---|---|---|
| 2003/0069329 A1* | 4/2003 | Kubota et al. | 523/160 |
| 2003/0091824 A1 | 5/2003 | Kim et al. | |
| 2004/0151910 A1 | 8/2004 | Koller et al. | |
| 2004/0156986 A1* | 8/2004 | Yadav | 427/180 |
| 2006/0165989 A1* | 7/2006 | Takikawa et al. | 428/402.2 |
| 2007/0280978 A1 | 12/2007 | Takada et al. | |
| 2008/0107977 A1 | 5/2008 | Hoshino et al. | |
| 2008/0152909 A1* | 6/2008 | Kyotani et al. | 428/402 |
| 2009/0283726 A1 | 11/2009 | Mizoguchi et al. | |

FOREIGN PATENT DOCUMENTS

| | | |
|---|---|---|
| EP | 1 291 370 A1 | 3/2003 |
| GB | 1156653 | 7/1969 |
| JP | 7-11150 A | 1/1995 |
| JP | 8-053568 A | 2/1996 |
| JP | 9-208437 A | 8/1997 |
| JP | 2003-73407 A | 3/2003 |
| JP | 2006-89389 A | 4/2006 |
| JP | 2006-169544 A | 6/2006 |
| JP | 2008-189814 A | 8/2008 |
| WO | WO 2006085596 A1 * | 8/2006 |
| WO | WO 2007060259 A2 * | 5/2007 |

OTHER PUBLICATIONS

European Patent Office, European Search Report for European Patent Application No. EP 09 01 1327, Jul. 19, 2010, European Patent Office, Munich, Germany.

Shim, J., et al., Zinc Oxide/Polymethylmethacrylate Composite Microspheres by In Situ Suspension Polymerization and their Morphological Study, Colloids and Surfaces A, vol. 207, 2002, pp. 105-111.

* cited by examiner

*Primary Examiner* — Dennis J Parad
(74) *Attorney, Agent, or Firm* — Hamre, Schumann, Mueller & Larson, P.C.

(57) ABSTRACT

Composite spherical polymer particles contain a nanoparticulate pigment having an average primary particle size of from 0.1 to 0.005 μm, a high molecular dispersant having adsorptive property to the nanoparticulate pigment, and a (meth) acrylic resin. The nanoparticulate pigment is enclosed in a dispersed state in the high molecular dispersant and (meth) acrylic resin. The content of the nanoparticulate pigment ranges from 5 to 70 wt % based on the composite spherical polymer particles. The composite spherical polymer particles have an average particle size of from 1 to 20 μm. A production process of the composite spherical polymer particles and cosmetics containing the composite spherical polymer particles are also disclosed.

9 Claims, 6 Drawing Sheets

COMPOSITE SPHERICAL POLYMER PARTICLES AND THEIR PRODUCTION PROCESS, AND COSMETICS USING THE SAME

CROSS-REFERENCE TO RELATED APPLICATION

This application claims the priority of Japanese Patent Application 2009-063292 filed Mar. 16, 2009, which is incorporated herein by reference.

BACKGROUND OF THE INVENTION

1. Field of the Invention

This invention relates to composite spherical polymer particles, which contain a nanoparticulate (ultrafine) pigment enclosed therein and are suited as a raw material for cosmetics. This invention is also concerned with their production process and cosmetics using them.

2. Description of the Related Art

In cosmetics, numerous powdery materials are used in view of their functions. Examples of such powdery materials include inorganic color pigments such as titanium oxide, red iron oxide, yellow iron oxide and black ion oxide, inorganic extender pigments such as kaolin, talc and mica, and tar colorants such as Red No. 202 (FDA Name: D&C Red No. 7; CI#: C.I. 15850), Red No. 226 (FDA Name: D&C Red No. 30; CI#: C.I. 73360) and Yellow No. 4 aluminum lake (FDA Name: FD&C: Yellow No. 5 aluminum lake; CI#: C.I. 19140 aluminum lake), and the like. Further, nanoparticles having an average particle size of 0.1 μm or smaller are also mixed in some powders to be added.

Titanium oxide and zinc oxide have conventionally been used in ultraviolet light screening materials. Nanoparticulate titanium oxide and zinc oxide having an average primary particle size of 0.1 μm or smaller are also equipped with high transparency in addition to ultraviolet light screening effect. Therefore, these nanoparticulate titanium oxide and zinc oxide are useful raw materials for UV protection cosmetics (see JP-A-08-053568 and JP-A-09-208437).

Of red iron oxide and yellow iron oxide, nanoparticles having an average primary particle size of 0.1 μm or smaller are called "transparent iron oxides", and despite their reduced concealing property, are used as brilliant color pigments of excellent transparency in cosmetics. Cosmetics using these pigments are reduced in concealing property, but give highly-transparent, color sensations and also natural finishes generally preferred by consumers. The above-described pigments are, therefore, suited as raw materials for cosmetics.

However, a nanoparticulate pigment subjected to ultrafine grinding to provide it with enhanced functionality is provided with an increased specific surface area and greater surface energy, and therefore, its primary particles are prone to aggregation. It is, hence, difficult to disperse the nanoparticulate pigment into primary particles. If a nanoparticulate pigment is used in the form of a secondary aggregate as a cosmetic raw material, the resulting cosmetic cannot fully exhibit the function which the nanoparticulate pigment is inherently equipped with. Even if such a nanoparticulate pigment is dispersed to primary particles and is then mixed with another cosmetic raw material, the primary particles of the nanoparticulate pigment tend to aggregate for their high surface energy. As a consequence, a cosmetic with a re-aggregated nanoparticulate pigment contained therein undergoes variations with time, and becomes defective in quality such as variations in hue, deteriorations in use feel, and reductions in storage stability (variations in viscosity, settlement, aggregation, discoloration). In addition, a nanoparticulate pigment the average primary particle size of which is 0.1 μm or smaller is so small that a cosmetic with the nanoparticulate pigment mixed therein is poor in spreadability. Further, a cosmetic containing a needle crystal material such as titanium oxide gives an unpleasant use feel as if pricked at the skin, and moreover, its cleansing properties are poor.

In recent years, there is an increasing worldwide concern about the safety of nanoparticles having an average primary particle size of 0.1 μm or smaller. Led by NEDO (New Energy and Industrial Technology Development Organization), a great deal of work is under way in Japan for the development of "a risk assessment of manufactured nanomaterials". As a cosmetic raw material, nanoparticles have raised a concern that they may give hazardous effects to human health, for example, that for their ability to penetrate through cytomembranes because of their ultrafine size, they may impair the barrier function of skin and not only may remain on the skin but also may penetrate into the body or that they may form active oxygen of high toxicity due to their catalytic action.

In addition, powdery materials for cosmetics, such as carbon black, silica and tar colorants, are also nanoparticles having an average primary particle size of 0.1 μm or smaller, and for similar reasons, there is a concern about their safety.

As has been described above, nanoparticles the average primary particle size of which is 0.1 μm or smaller are suited as a powdery cosmetic raw material, but are accompanied by drawbacks due to their physical and chemical properties, for example, unstable dispersibility, aggregability, thickening property, large specific surface area, high surface activity, hazardousness, and therefore, are inferior in handling ease. For the quality design of a cosmetic with nanoparticles mixed therein, significantly high technologies are thus required for dispersion stabilization, improved storage stability (minimization of viscosity variations, settlement or aggregation, and discoloration), an improved use feel, and the like.

SUMMARY OF THE INVENTION

The present inventor has enthusiastically investigated to develop a method that makes it possible to avoid the above-described hazardousness of a nanoparticulate pigment useful as a cosmetic raw material without impairing its functions as ultrafine particles. As a result, it was found that by dispersing and incorporating a nanoparticulate pigment in a (meth) acrylic resin in the presence of a high molecular dispersant having high adsorptive property to the pigment, composite spherical polymer particles of micron size can be obtained without impairing the functions of the nanoparticulate pigment as ultrafine particles, leading to the completion of the present invention.

In one aspect of the present invention, there is, accordingly, provided composite spherical polymer particles comprising a nanoparticulate pigment having an average primary particle size of from 0.1 to 0.005 μm, a high molecular dispersant having adsorptive property to the nanoparticulate pigment, and a (meth)acrylic resin. The nanoparticulate pigment is enclosed in a dispersed state in the high molecular dispersant and (meth)acrylic resin, a content of the nanoparticulate pigment ranges from 5 to 70 wt % based on the composite spherical polymer particles, and the composite spherical polymer particles have an average particle size of from 1 to 20 μm.

In the above-described composite spherical polymer particles, a content of the high molecular dispersant may preferably be from 5 to 100 wt % based on the nanoparticulate pigment; the (meth)acrylic resin may preferably be a polymer obtainable from at least one (meth)acrylic monomer selected from a group consisting of monofunctional hydrophobic (meth)acrylic monomers and polyfunctional hydrophobic (meth)acrylic monomers; and the polymer may preferably be obtainable from (A) at least one monofunctional hydrophobic (meth)acrylate ester and (B) at least one polyfunctional hydrophobic (meth)acrylate ester, and a weight ratio (A/B) of the at least one monofunctional hydrophobic (meth)acrylate ester (A) to the at least one polyfunctional hydrophobic (meth)acrylate ester (B) may preferably be from 0/100 to 50/50.

In another aspect of the present invention, there is also provided a process for producing composite spherical polymer particles. The process comprises subjecting a nanoparticulate pigment, which has an average primary particle size of from 0.1 to 0.005 μm, together with a hydrophobic (meth)acrylic monomer to dispersion mixing in a presence of a high molecular dispersant having adsorptive property to the nanoparticulate pigment, mixing the resulting dispersion into an aqueous medium, and then subjecting the resulting mixture to suspension polymerization.

In the above-described process, the high molecular dispersant may be used preferably in an amount of from 5 to 100 wt % based on the nanoparticulate pigment; the hydrophobic (meth)acrylic monomer may preferably be at least one (meth) acrylic monomer selected from a group consisting of monofunctional hydrophobic (meth)acrylic monomers and polyfunctional hydrophobic (meth)acrylic monomers; and preferably, (A) at least one monofunctional hydrophobic (meth)acrylate ester and (B) at least one polyfunctional hydrophobic (meth)acrylate ester may be used at a weight ratio (A/B) of from 0/100 to 50/50.

In a further aspect of the present invention, there is also provided a cosmetic comprising a cosmetic base and the above-described composite spherical polymer particles. In this cosmetic, a content of the composite spherical polymer particles may preferably be from 0.5 to 60 wt % based on the cosmetic base.

The cosmetic, which contains the composite spherical polymer particles of micron size obtainable as described above, can avoid the hazardousness of the nanoparticulate pigment attributable to its ultrafine size, because the nanoparticulate pigment is not mixed as it is but is enclosed in a uniformly dispersed state in polymer particles.

DETAILED DESCRIPTION OF THE INVENTION AND PREFERRED EMBODIMENTS

The composite spherical polymer particles and their production process and the cosmetic using the composite spherical polymer particles, all of which pertain to the present invention, will hereinafter be described in detail.

<Composite Spherical Polymer Particles>

As the composite spherical polymer particles according to the present invention are to be mixed in cosmetics, their average particle size may be preferably from 1 to 20 μm, more preferably from 1 to 15 μm. A cosmetic with composite spherical polymer particles having an unduly small average particle size and mixed therein is poor in spreadability, while a cosmetic with composite spherical polymer particles having an excessively large average particle size and mixed therein produces a foreign body sensation or the like and gives a poor use feel. The composite spherical polymer particles may preferably have shapes closer to true spheres from the standpoint of giving an excellent use feel, although no particular limitation is imposed on their shapes.

It is to be noted that the average particle size of the composite spherical polymer particles is a volume average diameter (median diameter) as measured by the electrical resistance method ("MULTISIZER 3", trade name; manufactured by Beckman Coulter, Inc.).

In the composite spherical polymer particles according to the present invention, the enclosed amount of the nanoparticulate pigment is from 5 to 70 wt %, preferably from 10 to 50 wt % based on the composite spherical polymer particles. An unduly small enclosed amount of the nanoparticulate pigment cannot exhibit the functions of the nanoparticulate pigment. On the other hand, the mixing of the nanoparticulate pigment in an unnecessarily large amount results in the enclosure of the nanoparticulate pigment in an aggregated state in the spherical polymer particles and cannot exhibit the functions of the nanoparticulate pigment, although there is a technical limitation to increasing the enclosed amount of the nanoparticulate pigment.

<Nanoparticulate Pigment>

The nanoparticulate pigment for use in the present invention has an average primary particle size (hereinafter simply called "average particle size") of from 0.1 to 0.005 μm, and may preferably be an ultrafinely divided inorganic pigment or a tar colorant. Examples of such an ultrafinely divided inorganic pigment include ultrafine titanium oxide, ultrafine zinc oxide, transparent red iron oxide, transparent yellow iron oxide, silica, titanium black, carbon black, and the like. Examples of the tar colorant include Red No. 202 (FDA Name: D&C Red No. 7; CI#: C.I. 15850), Red No. 226 (FDA Name: D&C Red No. 30; CI#: C.I. 73360), Yellow No. 4 aluminum lake (FDA Name: FD&C: Yellow No. 5 aluminum lake; CI#: C.I. 19140 aluminum lake), Yellow No. 5 aluminum lake (FDA Name: FD&C Yellow No. 6 aluminum lake; CI#: C.I. 15985 aluminum lake), Blue No. 1 aluminum lake (FDA Name: FD&C Blue No. 1 aluminum lake; CI#: C.I. 73015 aluminum lake), and the like.

<High Molecular Dispersant>

The high molecular dispersant for use in the present invention has high adsorptive property to the nanoparticulate pigment to be enclosed, and more specifically can be a high molecular dispersant of a molecular structure that has functional groups capable of adsorbing on particle surfaces of the nanoparticulate pigment to be enclosed and functional groups having high compatibility with the monomer as a dispersion medium. Desired is a high molecular dispersant having a polyurethane or poly (meth)acrylic molecular structure and a polystyrene equivalent weight average molecular weight of from 3,000 to 30,000, with from 5,000 to 20,000 being more preferred.

If the molecular weight of the high molecular dispersant is too low, it has low dispersion stabilizing property for the nanoparticulate pigment because its pigment adsorbing chains are short. If its molecular weight is too high, on the other hand, it becomes difficult to control the particle size of the composite spherical polymer particles to be formed because the use of the high molecular dispersant forms a dispersion having high viscosity. Commercial products of such a high molecular dispersant include, for example, "DISPER BYK-163", "DISPER BYK-170" and "DISPER BYK-2000" (all, trade names; products of Big Chemie Japan Corp.) and "EFKA-1101" and "EFKA-4310" (both, trade names; products of Ciba Specialties Chemicals Corp.).

Dispersion of the nanoparticulate pigment in the monomer in the presence of the high molecular dispersant provides a dispersion, which is high in concentration, is low in viscosity and is excellent in dispersion stability. By subjecting the dispersion to suspension polymerization in the aqueous medium, it is possible to obtain composite spherical polymer particles with the nanoparticulate pigment stably dispersed at high concentration in a uniform state therein.

If the high molecular dispersant does not exist or exists in an amount smaller than that needed upon enclosing the above-mentioned nanoparticulate pigment, the dispersion of the nanoparticulate pigment in the monomer cannot proceed to sufficient extent, and moreover, the high molecular dispersant cannot be adsorbed sufficiently on the particle surfaces of the nanoparticulate pigment and in the below-described production process, the charged nanoparticulate pigment cannot be enclosed in its entirety in the resulting (meth)acrylic resin.

Use of the high molecular dispersant in an excessively large amount, on the other hand, leads not only to the wasting of the high molecular dispersant, but also to a reduction in the proportion of the hydrophobic (meth)acrylic monomer component in the resulting (meth)acrylic resin, thereby providing the resultant spherical particles with reduced physical strength and also affecting the storage stability (viscosity stability, settling resistance, aggregation resistance, discoloration resistance) of a cosmetic in which the spherical particles are to be mixed. The amount of the high molecular dispersant to be used is from 5 to 100 wt %, preferably from 10 to 70 wt % based on the nanoparticulate pigment, although it differs depending on the particle size, surface properties and amount of the nanoparticulate pigment to be used.

<Monomer>

The monomer for use in the present invention is a hydrophobic (meth)acrylic monomer, and may preferably be at least one of monofunctional and polyfunctional, hydrophobic (meth)acrylate ester monomers.

The monofunctional hydrophobic (meth)acrylate ester monomers include, for example, hexyl (meth)acrylate, 2-ethylhexyl (meth)acrylate, t-octyl (meth)acrylate, isoamyl (meth)acrylate, decyl (meth)acrylate, isodecyl (meth)acrylate, stearyl (meth)acrylate, isostearyl (meth)acrylate, cyclohexyl (meth)acrylate, 4-n-butylcyclohexyl (meth)acrylate, bornyl (meth)acrylate, isobornyl (meth)acrylate, benzyl (meth)acrylate, 2-ethylhexyl diglycol (meth)acrylate, butoxyethyl (meth)acrylate, benzyl (meth)acrylate, butoxymethyl (meth)acrylate, 3-methoxybutyl (meth)acrylate, alkoxymethyl (meth)acrylates, alkoxyethyl (meth)acrylates, 2-(2-methoxyethoxy)ethyl (meth)acrylate, 2-(2-butoxyethoxy)ethyl (meth)acrylate, 4-butylphenyl (meth)acrylate, phenyl (meth)acrylate, 2,4,5-tetramethylphenyl (meth)acrylate, and EO-modified-2-ethylhexyl (meth)acrylates.

Monofunctional (meth)acrylate ester monomers of relatively high molecular weights are hydrophobic. The use of one or more of such hydrophobic monomers can reduce the formation of polymer particles that move into a water phase in the polymerization step and hence do not contain the nanoparticulate pigment, and therefore, is preferred.

The polyfunctional hydrophobic (meth)acrylate ester monomers include, for example, 1,6-hexanediol di(meth)acrylate, 1,10-decanediol di(meth)acrylate, neopentyl glycol di(meth)acrylate, 2,4-dimethyl-1,5-pentanediol di(meth)acrylate, butylethylpropanediol di(meth)acrylate, ethoxylated cyclohexanemethanol di(meth)acrylate, ethylene glycol di(meth)acrylate, 2-ethyl-2-butyl-butanediol di(meth)acrylate, 1,4-butanediol di(meth)acrylate, 2-ethyl-2-butyl-propanediol di(meth)acrylate, 1,9-nonane di(meth)acrylate, tricyclodecane di(meth)acrylate, trimethylolpropane tri(meth)acrylate, and pentaerythritol tetra(meth)acrylate.

When (A) at least one monofunctional hydrophobic (meth)acrylate ester and (B) at least one polyfunctional hydrophobic (meth)acrylate ester are used in combination, the use of the polyfunctional hydrophobic (meth)acrylate ester (B) in a greater proportion makes it possible to have the nanoparticulate pigment enclosed at a higher concentration in the resulting polymer particles and also to provide the resulting polymer particles with improved solvent resistance, and therefore, is preferred. The monofunctional hydrophobic (meth)acrylate ester (A) and the polyfunctional hydrophobic (meth)acrylate ester (B) may be used at a weight ratio (A/B) of preferably from 0/100 to 50/50, more preferably from 1/99 to 40/60.

<Production Process of Composite Spherical Polymer Particles>

A description will next be made of an illustrative procedure in the process to be practiced in the present invention for the production of the composite spherical polymer particles.

Firstly, the nanoparticulate pigment and high molecular dispersant are added to the monomer or monomer mixture. Subsequent to thoroughly stirring and mixing, the resulting mixture is subjected to dispersion processing to prepare a dispersion of the nanoparticulate pigment in the monomer or monomer mixture. Further, a fresh supply of the monomer or monomer mixture, in which a polymerization initiator has been dissolved beforehand, is added to the dispersion, followed by stirring and mixing to prepare a uniform polymerizable dispersion. The monomer or monomer mixture may be replaced in part by an organic solvent as needed.

Usable examples of the polymerization initiator for use in the present invention include peroxides such as lauryl peroxide, benzoyl peroxide and t-butyl peroxy(2-ethylhexanoate), and azo compounds such as 2,2'-azobis-(2,4-dimethylvaleronitrile).

A dispersion stabilizer (protective colloid) is next dissolved in deionized water to prepare an aqueous medium. The above-prepared polymerizable dispersion is mixed in the aqueous medium under stirring to obtain a suspension. Using an emulsification machine such as a homogenizer, the sizes of droplets of the polymerizable dispersion in the suspension are then adjusted. By changing the revolution speed of the emulsification machine to control its shear force, the polymerizable dispersion in the suspension can be easily formed into droplets of desired diameter.

The kind and concentration of the dispersion stabilizer should be chosen such that the suspended droplets formed by the emulsification machine would not develop inconvenience such as destruction or merger during their formation and/or their transfer into a polymerization system and/or in the course of the polymerization.

Examples of the dispersion stabilizer for use in the present invention include water-soluble high molecular substances such as methylcellulose, polyvinyl alcohol and sodium acrylate, and inorganic salts such as hydroxyapatite, tribasic calcium phosphate and calcium carbonate.

The suspension obtained as described above is then continuously heated at 60 to 80° C. for 3 to 10 hours to subject it to suspension polymerization. As a result, composite spherical polymer particles with the nanoparticulate pigment enclosed in an amount of from 5 to 70 wt %, preferably from 10 to 50 wt % based on the total weight of the composite spherical polymer particles are obtained. After completion of the polymerization reaction, the composite spherical polymer particles are separated from the aqueous medium by filtration, centrifugation or the like. Further, the dispersion stabilizer is eliminated through a washing step, and the composite spherical polymer particles are dried. The composite spherical polymer particles obtained in the form of an aggregate are then crushed to obtain them in the form of a powder.

<Cosmetic>

The cosmetic according to the present invention contains as essential ingredients the cosmetic base and the above-described composite spherical polymer particles of the present invention, and can be furnished in various forms such as liquid, solid and wax forms.

The content of the composite spherical polymer particles mixed in the cosmetic according to the present invention may be preferably from 0.5 to 60 wt %, more preferably from 2 to 40 wt % based on the cosmetic base. Examples of the cosmetic include basic skin care cosmetics and makeup cosmetics, such as sunscreens, foundations and mascaras.

In the cosmetic according to the present invention, it is possible to selectively use, in addition to the composite spherical polymer particles of the present invention, various powdery cosmetic bases, for example, titanium oxide, talc, sericite, pearlescent pigments and the like to extent not impairing the advantageous effects of the present invention. In addition, it is also possible to mix one or more of cosmetic additives commonly employed in cosmetics, such as water, oils and fats, silicone oils, surfactants, preservatives and fragrances, as needed.

EXAMPLES

The present invention will hereinafter be described more specifically based on examples and comparative examples, although the present invention shall by no means be limited to or by these examples. Further, the designations of "parts" and "%" to be described in the following examples are each on a weight basis. The particle sizes of ultrafine red iron oxide, ultrafine yellow iron oxide and yellow iron oxide are values measured from their electron micrographs, while the particle sizes of other particles are values converted by the BET method.

Example 1

| | |
|---|---|
| Ultrafine titanium oxide (average particle size: 0.01 μm) | 90 parts |
| High molecular dispersant ("DISPER BYK-170", purity: 30%) | 90 parts |
| Hexamethylene dimethacrylate | 100 parts |

The above-described ingredients were premixed, and were then dispersed in a bead mill to obtain a dispersion of the ultrafine titanium oxide. In a solution prepared beforehand by dissolving 2,2'-azobis-(2,4-dimethylvaleronitrile) (1 parts) in ethylene glycol dimethacrylate (55 parts), the dispersion of the ultrafine titanium oxide (185 parts) was mixed under stirring to prepare a uniform polymerizable monomer dispersion. In a water phase prepared by dissolving partially-saponified polyvinyl alcohol (35 parts) in deionized water (700 parts) placed in a different vessel, the polymerizable monomer dispersion was then mixed, followed by stirring at 10,000 rpm for 5 minutes in a homogenizer to obtain a uniform suspension. The suspension was observed under an optical microscope. As a result, the ultrafine titanium oxide was found in a dispersed state in suspended droplets of the polymerizable monomer dispersion, and further, the ultrafine titanium oxide was not found to have moved in the water phase.

Figure 1:
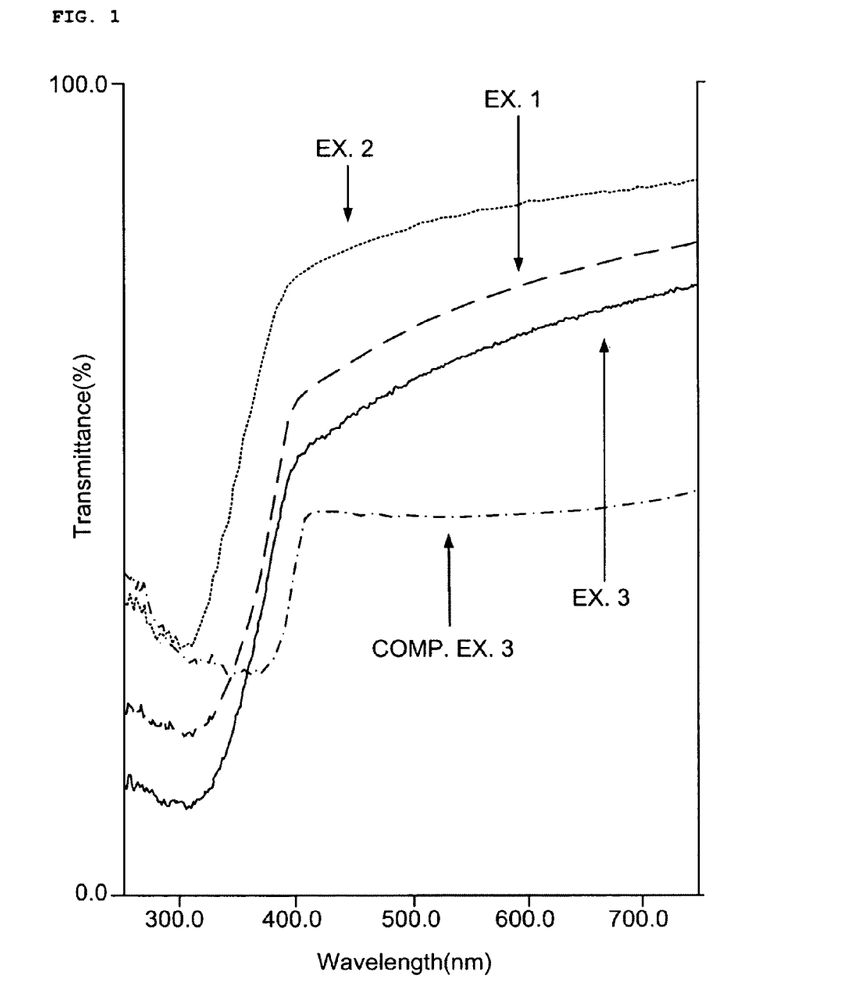
FIG. 1 shows UV-Vis transmission spectra of composite spherical polymer particles of Example 1, Example 2, Example 3 and Comparative Example 3.

In a polymerizer of a polymerization system equipped with a stirrer and a nitrogen gas inlet tube, the suspension was charged, and a polymerization reaction was then conducted continuously at 70° C. for 6 hours. The polymerization mixture was observed under an optical microscope. As a result, the ultrafine titanium oxide was not found in the water phase. After being allowed to cool, the resultant ultrafine particles were collected from the suspension by filtration, dried, and then subjected to crushing to obtain composite spherical polymer particles. It is appreciated from FIG. 1 that those composite spherical polymer particles were well-balanced between UV-B absorbing capacity and transparency.

Example 2

2,2'-Azobis-(2,4-dimethylvaleronitrile) (1.5 parts) was dissolved in a mixed monomer of hexamethylene dimethacrylate (20 parts), 2-ethylhexyl methacrylate (50 parts) and ethylene glycol dimethacrylate (35 parts). In the thus-prepared solution, an aliquot (125 parts) of the dispersion of the ultrafine titanium oxide as obtained above in Example 1 was mixed under stirring to prepare a uniform polymerizable monomer dispersion. Subsequently, operations were conducted as in Example 1 except that the stirring speed of the homogenizer was changed to 8,000 rpm, whereby composite spherical polymer particles were obtained. It is appreciated from FIG. 1 that those composite spherical polymer particles were high in transparency although they were inferior in UV-B absorbing capacity to those of Example 1.

Example 3

2,2'-Azobis-(2,4-dimethylvaleronitrile) (1 parts) was dissolved in a mixture of propylene glycol monomethylacetate (20 parts) and ethylene glycol dimethacrylate (7 parts). In the thus-prepared solution, an aliquot (250 parts) of the dispersion of the ultrafine titanium oxide as obtained above in Example 1 was mixed under stirring to prepare a uniform polymerizable monomer dispersion. Subsequently, operations were conducted as in Example 1 except that the stirring speed of the homogenizer was changed to 11,000 rpm, whereby composite spherical polymer particles were obtained. It is appreciated from FIG. 1 that those composite spherical polymer particles were slightly lower in transparency than those of Example 1 although they were superior in UV-B absorbing capacity to those of Example 1.

Example 4

| | |
|---|---|
| Ultrafine zinc oxide (average particle size: 0.025 μm) | 120 parts |
| High molecular dispersant ("DISPER BYK-170", purity: 30%) | 80 parts |
| Hexamethylene dimethacrylate | 40 parts |

Figure 2:
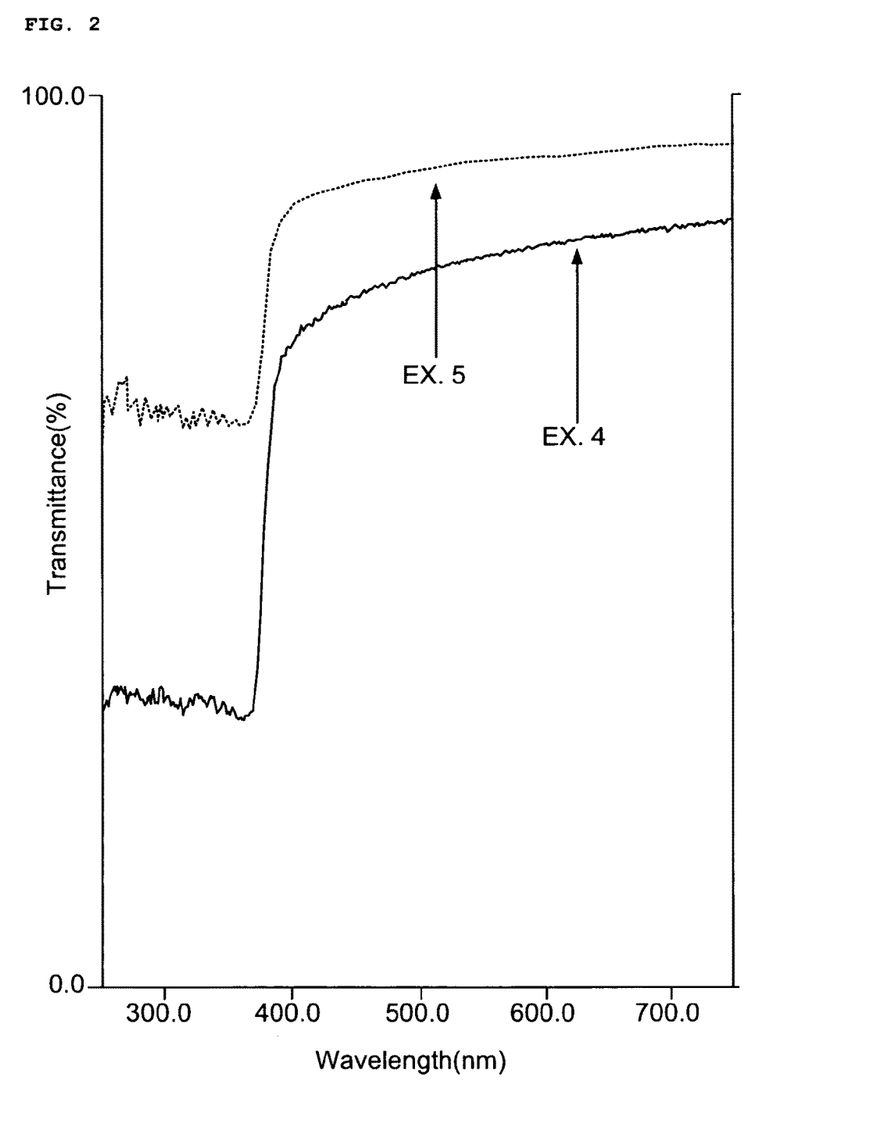
FIG. 2 shows UV-Vis transmission spectra of composite spherical polymer particles of Example 4 and Example 5.

The above-described ingredients were premixed, and were then dispersed in a bead mill to obtain a dispersion of the ultrafine zinc oxide. In a solution prepared beforehand by dissolving 2,2'-azobis-(2,4-dimethylvaleronitrile) (1 parts) in a mixed monomer of hexamethylene dimethacrylate (25 parts) and ethylene glycol dimethacrylate (50 parts), the dispersion of the ultrafine zinc oxide (160 parts) was mixed under stirring to prepare a uniform polymerizable monomer dispersion. Subsequently, operations were conducted as in Example 1, whereby composite spherical polymer particles were obtained. It is appreciated from FIG. 2 that those composite spherical polymer particles were well-balanced between UV-A absorbing capacity and transparency.

Example 5

2,2'-Azobis-(2,4-dimethylvaleronitrile) (1.2 parts) was dissolved in a mixed monomer of isobornyl methacrylate (80 parts), hexamethylene dimethacrylate (20 parts) and ethylene glycol dimethacrylate (40 parts). In the thus-prepared solution, an aliquot (80 parts) of the dispersion of the ultrafine zinc oxide as obtained above in Example 4 was mixed under stirring to prepare a uniform polymerizable monomer dispersion. Subsequently, operations were conducted as in Example 1 except that the stirring speed of the homogenizer was changed to 7,000 rpm, whereby composite spherical polymer particles were obtained. From FIG. 2, UV-A absorbing capacity can also be recognized on the composite spherical polymer particle.

Example 6

| | |
|---|---|
| Carbon black (average particle size: 0.013 µm) | 42 parts |
| High molecular dispersant ("DISPER BYK-163", purity: 45%) | 47 parts |
| Hexamethylene dimethacrylate | 80 parts |
| Propylene glycol monomethyl acetate | 23 parts |

Figure 3:
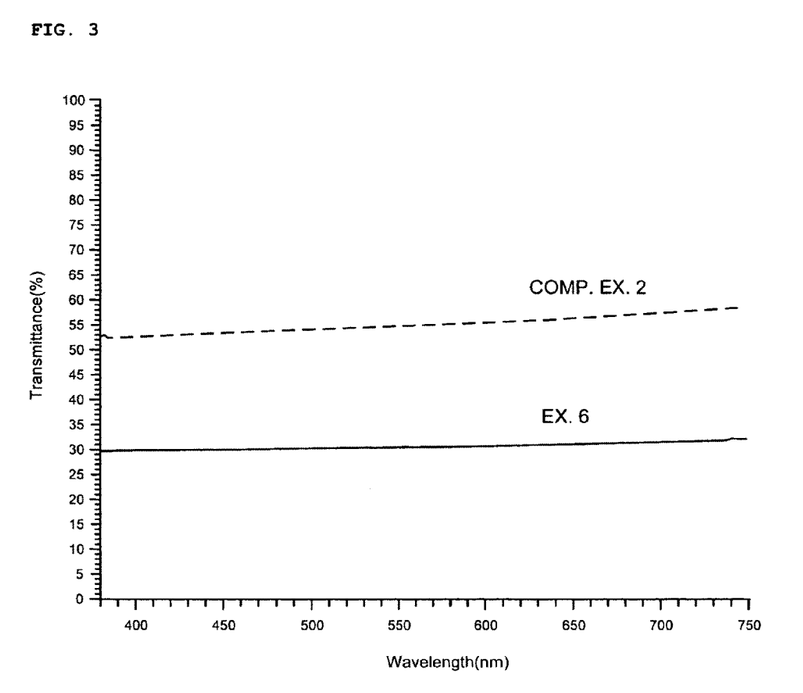
FIG. 3 shows Vis transmission spectra of composite spherical polymer particles of Example 6 and Comparative Example 2.

The above-described ingredients were premixed, and were then dispersed in a bead mill to obtain a dispersion of the carbon black. In a solution prepared beforehand by dissolving 2,2'-azobis-(2,4-dimethylvaleronitrile) (1.5 parts) in ethylene glycol dimethacrylate (78 parts), the dispersion of the carbon black (165 parts) was mixed under stirring to prepare a uniform polymerizable monomer dispersion. Subsequently, operations were conducted as in Example 1, whereby composite spherical polymer particles were obtained. It is appreciated from FIG. 3 that those composite spherical polymer particles were black particles having concealing property suited as a powdery cosmetic additive to be mixed in cosmetics. It is also appreciated from FIG. 5 that the carbon black was uniformly dispersed in those particles.

Example 7

| | |
|---|---|
| Ultrafine red iron oxide (average major particle size: 0.05 µm, average minor particle size: 0.01 µm) | 80 parts |
| High molecular dispersant ("EFKA-4310", purity: 40%) | 60 parts |
| Hexamethylene dimethacrylate | 100 parts |
| Propylene glycol monomethyl acetate | 20 parts |

Figure 4:
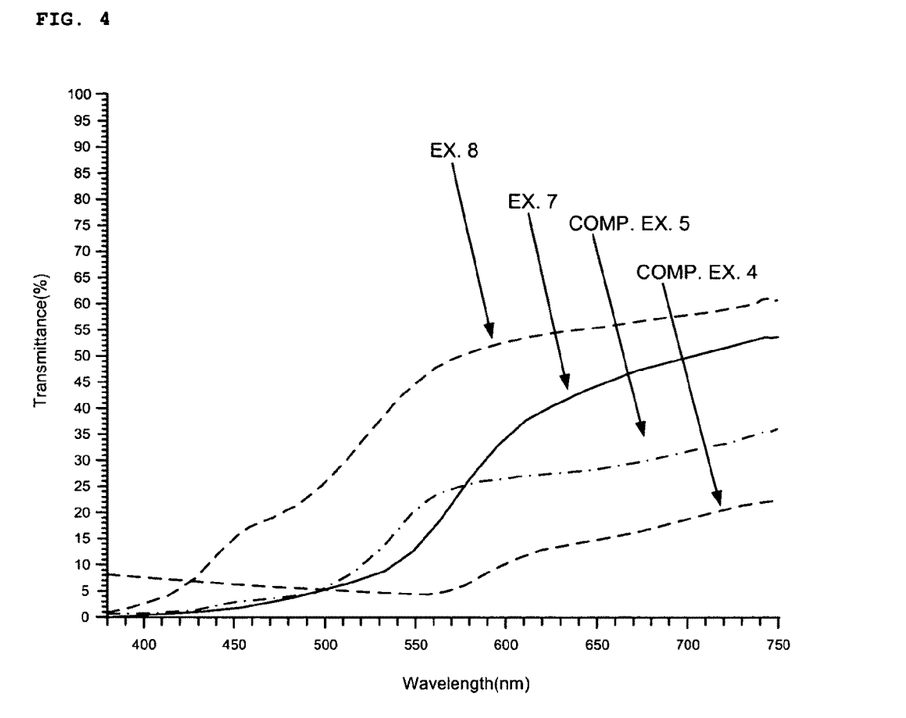
FIG. 4 shows Vis transmission spectra of composite spherical polymer particles of Example 7, Example 8, Comparative Example 4 and Comparative Example 5.

The above-described ingredients were premixed, and were then dispersed in a bead mill to obtain a dispersion of the ultrafine red iron oxide. In a solution prepared beforehand by dissolving 2,2'-azobis-(2,4-dimethylvaleronitrile) (1.2 parts) in 2-ethylhexylmethacrylate (47 parts), the dispersion of the ultrafine red iron oxide (195 parts) was mixed under stirring to prepare a uniform polymerizable monomer dispersion. Subsequently, operations were conducted as in Example 1 except that the stirring speed of the homogenizer was changed to 9,000 rpm, whereby composite spherical polymer particles were obtained. It is appreciated from FIG. 4 that those composite spherical polymer particles were red particles of micron size having the function of high transparency inherent to the ultrafine red iron oxide.

Example 8

| | |
|---|---|
| Ultrafine yellow iron oxide (average major particle size: 0.07 µm, average minor particle size: 0.01 µm) | 100 parts |
| High molecular dispersant ("EFKA-4310", purity: 40%) | 75 parts |
| Hexamethylene dimethacrylate | 80 parts |
| Propylene glycol monomethyl acetate | 25 parts |

The above-described ingredients were premixed, and were then dispersed in a bead mill to obtain a dispersion of the ultrafine yellow iron oxide. In a solution prepared beforehand by dissolving 2,2'-azobis-(2,4-dimethylvaleronitrile) (1 parts) in 2-ethylhexyl methacrylate (32 parts), the dispersion of the ultrafine yellow iron oxide (224 parts) was mixed under stirring to prepare a uniform polymerizable monomer dispersion. Subsequently, operations were conducted as in Example 1 except that the stirring speed of the homogenizer was changed to 85,000 rpm, whereby composite spherical polymer particles were obtained. It is appreciated from FIG. 4 that those composite spherical polymer particles were yellow particles of micron size having the function of high transparency inherent to the ultrafine yellow iron oxide.

Example 9

| | |
|---|---|
| Ultrafine titanium oxide (average particle size: 0.01 µm) | 30 parts |
| High molecular dispersant ("DISPER BYK-170", purity: 30%) | 10 parts |
| Hexamethylene dimethacrylate | 200 parts |

Figure 5:
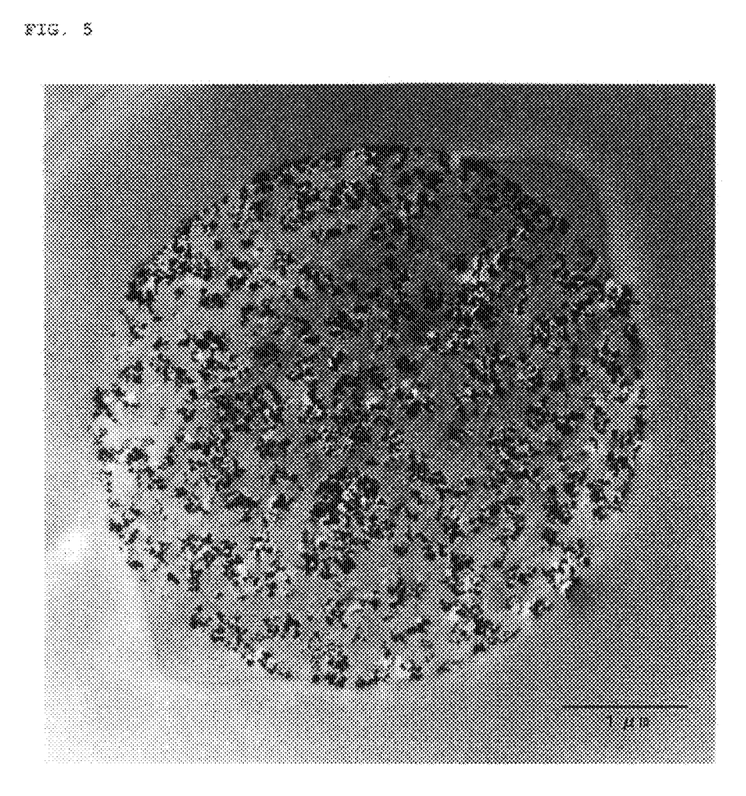
FIG. 5 shows a transmission electron micrograph of the composite spherical polymer particles of Example 6.

The above-described ingredients were dispersed on a paint shaker to obtain a dispersion of the ultrafine titanium oxide. In a solution prepared beforehand by dissolving 2,2'-azobis-(2,4-dimethylvaleronitrile) (1.8 parts) in 2-ethylhexyl methacrylate (45 parts), the dispersion of the ultrafine titanium oxide (160 parts) was mixed under stirring to prepare a uniform polymerizable monomer dispersion. Different from Comparative Example 1, the polymerizable monomer dispersion had been uniformly dispersed. Subsequently, operations were conducted as in Example 1 except that the stirring speed of the homogenizer was changed to 8,000 rpm, whereby a uniform suspension was obtained. The suspension was observed under an optical microscope. As a result, the ultrafine titanium oxide was found in suspended droplets of the polymerizable monomer dispersion, but some of the ultrafine titanium oxide was found to have moved in a water phase. Heat polymerization was conducted as in Example 1 to obtain composite spherical polymer particles. As shown in FIG. 5, however, some of the ultrafine titanium oxide was not enclosed, but adhered on the surfaces of the composite spherical polymer particles. The composite spherical polymer particles were as intended in the present invention, but were not considered to be sufficient in quality because the used amount of the high molecular dispersant was a little insufficient.

Comparative Example 1

| Ultrafine titanium oxide | 40 parts |
|---|---|
| (average particle size: 0.01 μm) | |
| Hexamethylene dimethacrylate | 260 parts |

The above-described ingredients were dispersed on a paint shaker to obtain a dispersion of the ultrafine titanium oxide. In a solution prepared beforehand by dissolving 2,2'-azobis-(2, 4-dimethylvaleronitrile) (1.8 parts) in 2-ethylhexyl methacrylate (50 parts), the dispersion of the ultrafine titanium oxide (150 parts) was mixed under stirring to prepare a polymerizable monomer dispersion. The polymerizable monomer dispersion had not been uniformly dispersed because no high molecular dispersant existed. Subsequently, operations were conducted as in Example 1 except that the stirring speed of the homogenizer was changed to 8,000 rpm, whereby a suspension was obtained. The suspension was observed under an optical microscope. As a result, the ultrafine titanium oxide was not found in suspended droplets of the polymerizable monomer dispersion, but was found to have moved in a water phase. Heat polymerization was conducted as in Example 1. Spherical polymer particles were obtained, but the ultrafine titanium oxide was not enclosed and adhered on the surfaces of the spherical polymer particles. It was unable to obtain composite spherical polymer particles as intended in the present invention.

Comparative Example 2

| Carbon black | 12 parts |
|---|---|
| (average particle size: 0.013 μm) | |
| Hexamethylene dimethacrylate | 138 parts |

The above-described ingredients were premixed, and were then dispersed in a bead mill to obtain a dispersion of the carbon black. In a solution prepared beforehand by dissolving 2,2'-azobis-(2,4-dimethylvaleronitrile) (2 parts) in ethylene glycol dimethacrylate (100 parts), the dispersion of the carbon black (100 parts) was mixed under stirring to prepare a polymerizable monomer dispersion. Subsequently, operations were conducted as in Example 1 except that the stirring speed of the homogenizer was changed to 8,000 rpm, whereby composite spherical polymer particles were obtained. As no high molecular dispersant existed, it was unable to disperse the carbon black to high concentration, and hence, to increase the enclosed amount of the carbon black. The composite spherical polymer particles were, therefore, provided with low concealing property. It is appreciated from FIG. 3 that those composite spherical polymer particles were black particles having a substantially lower transmittance than those of Example 6 and unsuited as a powdery cosmetic additive to be mixed in cosmetics.

Comparative Example 3

| Titanium oxide | 80 parts |
|---|---|
| (average particle size: 0.26 μm) | |
| High molecular dispersant | 80 parts |
| ("DISPER BYK-170", purity: 30%) | |
| Hexamethylene dimethacrylate | 100 parts |

The above-described ingredients were dispersed on a paint shaker to obtain a dispersion of the titanium oxide. In a solution prepared beforehand by dissolving 2,2'-azobis-(2,4-dimethylvaleronitrile) (1.2 parts) in ethylene glycol dimethacrylate (47 parts), the dispersion of the titanium oxide (195 parts) was mixed under stirring to prepare a uniform polymerizable monomer dispersion. Subsequently, operations were conducted as in Example 1 except that the stirring speed of the homogenizer was changed to 7,000 rpm, whereby composite spherical polymer particles were obtained. It is appreciated from FIG. 1 that those composite spherical polymer particles were inferior in UV absorbing capacity and low in transparency. Under the conditions of Comparative Example 3, it is impossible to obtain transparent particles having excellent UV absorbing property and the functions inherent to the nanoparticulate pigment like the composite spherical polymer particles of Example 1.

Comparative Example 4

| Red iron oxide | 80 parts |
|---|---|
| (average particle size: 0.16 μm) | |
| High molecular dispersant | 60 parts |
| ("EFKA-4310", purity: 40%) | |
| Hexamethylene dimethacrylate | 100 parts |

The above-described ingredients were premixed, and were then dispersed in a bead mill to obtain a dispersion of the red iron oxide. In a solution prepared beforehand by dissolving 2,2'-azobis-(2,4-dimethylvaleronitrile) (1.2 parts) in 2-ethylhexyl methacrylate (47 parts), the dispersion of the red iron oxide (180 parts) was mixed under stirring to prepare a uniform polymerizable monomer dispersion. Subsequently, operations were conducted as in Example 1 except that the stirring speed of the homogenizer was changed to 9,000 rpm, whereby composite spherical polymer particles were obtained. It is appreciated from FIG. 4 that different from Example 7, those composite spherical polymer particles were not transparent red particles having the functions inherent to a nanoparticulate pigment.

Comparative Example 5

| Yellow iron oxide | 100 parts |
|---|---|
| (average major particle size: 0.7 μm, | |
| average minor particle size: 0.07 μm) | |
| High molecular dispersant | 75 parts |
| ("EFKA-4310", purity: 40%) | |
| Hexamethylene dimethacrylate | 80 parts |

The above-described ingredients were premixed, and were then dispersed in a bead mill to obtain a dispersion of the yellow iron oxide. In a solution prepared beforehand by dissolving 2,2'-azobis-(2,4-dimethylvaleronitrile) (1 parts) in 2-ethylhexyl methacrylate (32 parts), the dispersion of the yellow iron oxide (204 parts) was mixed under stirring to prepare a uniform polymerizable monomer dispersion. Subsequently, operations were conducted as in Example 1 except that the stirring speed of the homogenizer was changed to 85,000 rpm, whereby composite spherical polymer particles were obtained. It is appreciated from FIG. 4 that different from Example 8, those composite spherical polymer particles were not transparent yellow particles having the functions inherent to the nanoparticulate pigment.

Comparative Example 6

| | |
|---|---|
| Ultrafine titanium oxide (average particle size: 0.01 μm) | 90 parts |
| Anionic surfactant (dipolyoxyethylene(8) $C_{12-15}$-alkyl ether phosphate) | 27 parts |
| Methyl methacrylate | 147 parts |

The above-described ingredients were premixed, and were then dispersed in a bead mill to obtain a dispersion of the ultrafine titanium oxide. In a solution prepared beforehand by dissolving 2,2'-azobis-(2,4-dimethylvaleronitrile) (1 parts) in ethylene glycol dimethacrylate (24 parts), the dispersion of the ultrafine titanium oxide (176 parts) was mixed under stirring to prepare a polymerizable monomer dispersion. Subsequently, operations were conducted as in Example 1, whereby a suspension was obtained. The suspension was observed under an optical microscope. As a result, the ultrafine titanium oxide was found in suspended droplets of the polymerizable monomer dispersion, but some of the ultrafine titanium oxide was found to have moved in a water phase. Heat polymerization was conducted as in Example 1. Composite spherical polymer particles were obtained. However, some of the ultrafine titanium oxide was not enclosed, but adhered on the surfaces of the composite spherical polymer particles. With the anionic surfactant, the hydrophobization of the ultrafine titanium oxide by adsorption was insufficient. It was, therefore, unable to have the ultrafine titanium oxide enclosed to such high concentration as in Example 1 and to obtain composite spherical polymer particles as intended in the present invention.

The compositions and average particle sizes of the particles obtained in the examples and comparative examples are shown in Table 1 to Table 3. It is to be noted that all the numerical values in the tables are expressed in terms of wt % except for the average particle sizes.

TABLE 1

Compositions of particles

| | Example 1 | Example 2 | Example 3 | Example 4 | Example 5 |
|---|---|---|---|---|---|
| Ultrafine titanium oxide | 30 | 20 | 40 | — | — |
| Ultrafine zinc oxide | — | — | — | 40 | 20 |
| Titanium oxide | — | — | — | — | — |
| Carbon black | — | — | — | — | — |
| Ultrafine red iron oxide | — | — | — | — | — |
| Ultrafine yellow iron oxide | — | — | — | — | — |
| Red iron oxide | — | — | — | — | — |
| Yellow iron oxide | — | — | — | — | — |
| High molecular dispersant | 9 | 6 | 12 | 8 | 4 |
| Anionic surfactant | — | — | — | — | — |
| Acrylic polymer | 61 | 74 | 48 | 52 | 76 |
| Average particle size, μm | 2.1 | 2.5 | 2.3 | 1.9 | 2.0 |

TABLE 2

Compositions of particles

| | Example 6 | Example 7 | Example 8 | Example 9 | Comp. Ex. 1 |
|---|---|---|---|---|---|
| Ultrafine titanium oxide | — | — | — | 10 | 10 |
| Ultrafine zinc oxide | — | — | — | — | — |
| Titanium oxide | — | — | — | — | — |
| Carbon black | 18 | — | — | — | — |
| Ultrafine red iron oxide | — | 30 | — | — | — |
| Ultrafine yellow iron oxide | — | — | 40 | — | — |
| Red iron oxide | — | — | — | — | — |
| Yellow iron oxide | — | — | — | — | — |
| High molecular dispersant | 9 | 9 | 12 | 1 | — |
| Anionic surfactant | — | — | — | — | — |
| Acrylic polymer | 73 | 61 | 48 | 89 | 90 |
| Average particle size, μm | 2.3 | 1.6 | 1.9 | 15 | — |

TABLE 3

| Compositions of particles | | | | | |
|---|---|---|---|---|---|
| | Comp. Ex. 2 | Comp. Ex. 3 | Comp. Ex. 4 | Comp. Ex. 5 | Comp. Ex. 6 |
| Ultrafine titanium oxide | — | — | — | — | 30 |
| Ultrafine zinc oxide | — | — | — | — | — |
| Titanium oxide | — | 30 | — | — | — |
| Carbon black | 4 | — | — | — | — |
| Ultrafine red iron oxide | — | — | — | — | — |
| Ultrafine yellow iron oxide | — | — | — | — | — |
| Red iron oxide | — | — | 30 | — | — |
| Yellow iron oxide | — | — | — | 40 | — |
| High molecular dispersant | — | 3 | 9 | 12 | — |
| Anionic surfactant | — | — | — | — | 9 |
| Acrylic polymer | 96 | 67 | 61 | 48 | 61 |
| Average particle size, μm | 2.5 | 2.1 | 2.2 | 1.7 | — |

Example 10

Formula

| | |
|---|---|
| (1) Particles of Example 1 | 4.5 parts |
| (2) Particles of Example 4 | 12 parts |
| (3) Polyoxysorbitol monolanolin acid ester | 3 parts |
| (4) Sorbitan sesquioleate | 7 parts |
| (5) Silicone oil | 20 parts |
| (6) Squalane | 18.5 parts |
| (7) Purified water | 30 parts |
| (8) 1,3-Butanediol | 5 parts |

Procedure

Figure 6:
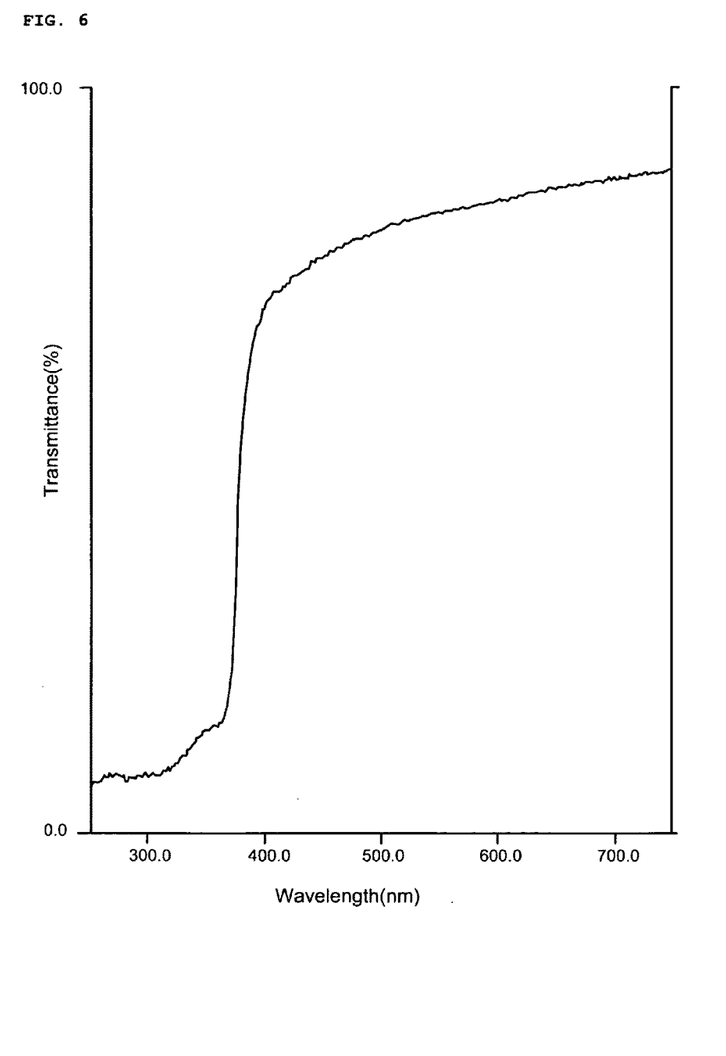
FIG. 6 shows a UV-Vis transmission spectrum of a sunscreen lotion of Example 10.

The ingredients (3) to (6) were heated to 65° C. to obtain an oily mixture. Under stirring by a stirrer, the ingredients (1) and (2) were mixed into the oily mixture to prepare a uniform oil-phase part. The ingredients (7) and (8) were heated to 65° C. to prepare a water-phase part. While stirring the oil-phase part by the stirrer, the water-phase part was added. Subsequent to emulsification, the resulting emulsion was allowed to cool so that a sunscreen lotion was obtained. The thus-obtained lotion was applied at 7.18 g/m² onto a quartz plate, and its UV-Vis transmittance was measured by a spectrophotometer. The resulting UV-Vis transmittance spectrum is shown in FIG. 6. It is appreciated from FIG. 6 that the sunscreen lotion had high transmittance for visible light and high screening effect for both ultraviolet light A and B. This indicates that the combined incorporation of high-transparency nanoparticulate pigments, such as ultrafine titanium oxide and ultrafine zinc oxide, in the forms of composite spherical polymer particles can produce a sunscreen lotion free of the hazardousness of such nanoparticulate pigments.

Example 11

Formula

| | |
|---|---|
| (1) Silicone-treated talc | 18.7 parts |
| (2) Silicone-treated mica | 38 parts |
| (3) Silicone-treated titanium oxide | 20 parts |
| (4) Particles of Example 7 | 3 parts |
| (5) Particles of Example 8 | 8 parts |
| (6) Particles of Example 6 | 0.3 parts ' |
| (7) Squalane | 6 parts |
| (8) Lanolin | 1 parts |
| (9) Decaglyceryl pentaoleate | 5 parts |

Procedure

The ingredients (1) to (6) were mixed, ground, and then placed in a blender. The ingredients (7) to (9) were added further, and in the blender, all the ingredients (1) to (9) were processed into a uniform mixture. The mixture was placed in a predetermined medium-size pan, and was then compression-molded to obtain a powder foundation in the form of a molded cake. The molded cake was measured at a surface thereof by a spectrophotometer. As a result, the following coordinate values were obtained on the L*a*h* colorimetric system: L* value, 74.7; a* value, 7.0; b* value, 18.4. This indicates that the combined incorporation of nanoparticulate pigments, such as ultrafine red iron oxide, ultrafine yellow iron oxide and carbon black, in the forms of composite spherical polymer particles can produce a powder foundation free of the hazardousness of such nanoparticulate pigments.

Example 12

Formula

| | |
|---|---|
| (1) Acrylic resin emulsion (solid content: 50%) | 40 parts |
| (2) Polyvinylpyrrolidone | 3 parts |
| (3) Particles of Example 6 | 15 parts |
| (4) 1,3-Butanediol | 5 parts |
| (5) Purified water | 37 parts |

Procedure

While stirring a mixture of the ingredients (4) and (5), the ingredient (2) was gradually added in small portions to dissolve it. After the ingredient (3) was added and uniformly dispersed under stirring, the ingredient (1) was added under stirring to obtain a uniform mixture as a mascara. This indicates that the incorporation of a nanoparticulate pigment, such as carbon black, in the form of composite spherical polymer particles can produce a mascara free of the hazardousness of such a nanoparticulate pigment.

The invention claimed is:

1. Composite spherical polymer particles used as a raw material for cosmetics comprising:
   a nanoparticulate pigment having an average primary particle size in a range from 0.1 to 0.005 μm;
   a (meth)acrylic resin that is a polymer obtained from a combination of monomer (A) and monomer (B) or the monomer (B) alone,
      wherein the monomer (A) is at least one monofunctional hydrophobic (meth)acrylate ester monomer, and the monomer (B) is at least one polyfunctional hydrophobic (meth)acrylate ester monomer, wherein said at least one polyfunctional hydrophobic (meth)acrylate ester monomers comprises at least two (meth)acrylate ester functional groups, and a weight ratio (A/B) of the at least one monofunctional hydrophobic (meth)acrylate ester monomer (A) to the at least one polyfunctional hydrophobic (meth)acrylate ester monomer (B) is in a range from 0/100 to 80/73; and a dispersant having a polyurethane structure or a poly(meth)acrylic molecular structure, a polystyrene equivalent weight average molecular weight from 3,000 to 30,000, functional groups capable of adsorbing on particle surfaces of the nanoparticulate pigment, and functional groups having compatibility with the monomers as a dispersion medium, wherein the composite spherical polymer particles are formed of the nanoparticulate pigment incorporated in a uniformly dispersed state in the (meth)acrylic resin in the presence of the dispersant, a content of the nanoparticulate pigment ranges from 5 to 70 wt % relative to the composite spherical polymer particles, the composite spherical polymer particles have an average particle size from 1 to 20 μm, and the composite spherical polymer particles have light transmittance in a range from about 50 to about 95% measured at a wavelength range from 390 to 750 nm when the composite spherical polymer particles include nanoparticulate titanium oxide or nanoparticulate zinc oxide as the nanoparticulate pigment in an amount in a range from 20 to 40 mass %.

2. The composite spherical polymer particles according to claim 1, wherein a content of the dispersant is from 5 to 100 wt % based on the nanoparticulate pigment.

3. A cosmetic comprising a cosmetic base and the composite spherical polymer particles according to claim 1.

4. The cosmetic according to claim 3, wherein a content of the composite spherical polymer particles is from 0.5 to 60 wt % based on the cosmetic base.

5. The composite spherical polymer particles according to claim 1, wherein the dispersant has the polyurethane molecular structure, and the polyurethane structure comprises at least an amino group.

6. The composite spherical polymer particles according to claim 1, wherein the dispersant has the poly(meth)acrylic molecular structure, and the poly(meth)acrylic molecular structure comprises at least an amino group or a quaternary ammonium salt.

7. The composite spherical polymer particles according to claim 1, wherein said at least one polyfunctional hydrophobic (meth)acrylate ester monomer is at least one selected from the group consisting of 1,6-hexanediol di(meth)acrylate, 1,10-decanediol di(meth)acrylate, neopentyl glycol di(meth)acrylate, 2,4-dimethyl-1,5-pentanediol di(meth)acrylate, butylethylpropanediol di(meth)acrylate, ethoxylated cyclohexanemethanol di(meth)acrylate, ethylene glycol di(meth)acrylate, 2-ethyl-2-butyl-butanediol di(meth)acrylate, 1,4-butanediol di(meth)acrylate, 2-ethyl-2-butyl-propanediol di(meth)acrylate, 1,9-nonane di(meth)acrylate, tricyclodecane di(meth)acrylate, trimethylolpropane tri(meth)acrylate, and pentaerythritol tetra(meth)acrylate.

8. A process for producing composite spherical polymer particles according to claim 1, which comprises:
subjecting a nanoparticulate pigment, which has an average primary particle size in a range from 0.1 to 0.005 μm, together with a combination of a hydrophobic (meth)acrylic monomer (A) and a hydrophobic (meth)acrylic monomer (B) or with the hydrophobic (meth)acrylic monomer (B) alone to dispersion mixing in a presence of a high molecular dispersant having adsorptive property to the nanoparticulate pigment, wherein the hydrophobic (meth)acrylic monomer (A) is at least one monofunctional hydrophobic (meth)acrylate ester monomer, and the hydrophobic (meth)acrylic monomer (B) is at least one polyfunctional hydrophobic (meth)acrylate ester monomer, wherein said at least one polyfunctional hydrophobic (meth)acrylate ester monomer comprises at least two (meth)acrylate ester functional groups, and a weight ratio (A/B) of the at least one monofunctional hydrophobic (meth)acrylate ester monomer (A) to the at least one polyfunctional hydrophobic (meth)acrylate ester monomer (B) is in a range from 0/100 to 80/73, and wherein the high molecular dispersant has a polyurethane structure or a poly(meth)acrylic molecular structure, a polystyrene equivalent weight average molecular weight from 3,000 to 30,000, functional groups capable of adsorbing on particle surfaces of the nanoparticulate pigment, and functional groups having compatibility with the monomers as a dispersion medium;

mixing the resulting dispersion into an aqueous medium; and then subjecting the resulting mixture to suspension polymerization, wherein the composite spherical polymer particles have light transmittance in a range from about 50 to about 95% measured at a wavelength range from 390 to 750 nm when the composite spherical polymer particles include nanoparticulate titanium oxide or nanoparticulate zinc oxide as the nanoparticulate pigment in an amount in a range from 20 to 40 mass %.

9. The process according to claim 8, wherein the high molecular dispersant is used in an amount of from 5 to 100 wt % based on the nanoparticulate pigment.

* * * * *